(12) United States Patent
Fujimori et al.

(10) Patent No.: US 9,549,949 B2
(45) Date of Patent: *Jan. 24, 2017

(54) ANTIVIRAL AGENT

(75) Inventors: Yoshie Fujimori, Tokyo (JP); Tsuruo Nakayama, Tokyo (JP); Tetsuya Sato, Tokyo (JP)

(73) Assignee: NBC MESHTEC, INC., Tokyo (JP)

( * ) Notice: Subject to any disclaimer, the term of this patent is extended or adjusted under 35 U.S.C. 154(b) by 230 days.

This patent is subject to a terminal disclaimer.

(21) Appl. No.: 13/061,760

(22) PCT Filed: Aug. 31, 2009

(86) PCT No.: PCT/JP2009/004264
§ 371 (c)(1),
(2), (4) Date: Apr. 5, 2011

(87) PCT Pub. No.: WO2010/026730
PCT Pub. Date: Mar. 11, 2010

(65) Prior Publication Data
US 2011/0195108 A1 Aug. 11, 2011

(30) Foreign Application Priority Data

Sep. 3, 2008 (JP) ................. 2008-226450
Oct. 8, 2008 (JP) ................. 2008-261877

(51) Int. Cl.
*A61K 33/18* (2006.01)
*A61K 9/10* (2006.01)
*A61K 33/24* (2006.01)
*A61K 33/34* (2006.01)
*A61K 9/51* (2006.01)

(52) U.S. Cl.
CPC ............... *A61K 33/18* (2013.01); *A61K 9/10* (2013.01); *A61K 9/5184* (2013.01); *A61K 33/24* (2013.01); *A61K 33/34* (2013.01)

(58) Field of Classification Search
CPC ........ A61K 9/10; A61K 9/5184; A61K 33/18; A61K 33/24; A61K 33/34
See application file for complete search history.

(56) References Cited

U.S. PATENT DOCUMENTS

| 6,451,333 | B1 |   | 9/2002  | Beerse et al.  |           |
|-----------|----|---|---------|----------------|-----------|
| 6,475,501 | B1 | * | 11/2002 | Kelly et al.   | 424/404   |
| 9,045,855 | B2 | * | 6/2015  | Fujimori       | A01N 25/34|
| 9,155,309 | B2 | * | 10/2015 | Fujimori       | A61L 31/16|
| 2005/0048131 | A1 |   | 3/2005  | Gabbay         |           |
| 2005/0123589 | A1 |   | 6/2005  | Gabbay         |           |
| 2006/0141015 | A1 | * | 6/2006  | Tessier et al. | 424/443   |

FOREIGN PATENT DOCUMENTS

| JP | 9-323935      |    | 12/1997  |           |
|----|---------------|----|----------|-----------|
| JP | 2002-338481   |    | 11/2002  |           |
| JP | 2005-160494   |    | 6/2005   |           |
| JP | 2006-188499   |    | 7/2006   |           |
| JP | 2008-138323   |    | 6/2008   |           |
| JP | 2009-072430   |    | 4/2009   |           |
| WO | WO 9639144 A1 | *  | 12/1996  | A61K 31/30|
| WO | 01/28337      |    | 4/2001   |           |
| WO | 01/74166      |    | 10/2001  |           |
| WO | 2005/083171   |    | 9/2005   |           |
| WO | 2007/093808   |    | 8/2007   |           |

OTHER PUBLICATIONS

International Search Report issued Oct. 27, 2009 in International (PCT) Application No. PCT/JP2009/004264.
English translation of International Preliminary Report on Patentability and Written Opinion dated Apr. 12, 2011.
Extended European Search Report dated Sep. 9, 2014 issued in corresponding European Patent Application No. 14165960.7.
Fyodorov, D.G., et al, "Inactivation of viruses of different taxonomic groups by cuprous sulphated", BIOSIS [Online] Biosciences Information Services, Jul. 2004.
Borkow, Gadi, et al., "Copper as a Biocidal Tool", Current Medicinal Chemistry, vol. 12, No. 18, Aug. 1, 2005, pp. 2163-2175.

* cited by examiner

*Primary Examiner* — Michael B Pallay
(74) *Attorney, Agent, or Firm* — Wenderoth, Lind & Ponack, L.L.P.

(57) ABSTRACT

An antiviral agent that contains as an active ingredient a particle of at least one kind of iodide composed of iodine and an element shown in Period 4 to Period 6 and Group 8 to Group 15 of a periodic table or at least one kind of monovalent copper compound. The antiviral agent can be incorporated into a variety of products. The antiviral agent can inactivate a wide range of viruses. The antiviral agent can be designed at a higher degree of freedom in terms of its constituents as compared to conventional antiviral agents. In addition, the antiviral agent can readily exhibit and maintain its antiviral activity because it does not require any pretreatments or special washing processes.

6 Claims, No Drawings

ANTIVIRAL AGENT

This application is a U.S. national stage of International Application No. PCT/JP2009/004264 filed Aug. 31, 2009.

TECHNICAL FIELD

The present invention relates to antiviral agents that can inactivate a wide range of viruses.

BACKGROUND ART

In recent years, increasing cases of deaths caused by viral infections such as SARS (severe acute respiratory syndrome), norovirus, and avian influenza have been reported. The prospect of a pandemic is now posing a worldwide threat due to ever more advanced transportation networks and continuously mutating viruses. The emergence of new influenza viruses is also an urgent issue that requires immediate action. Although the development of antiviral vaccines is one solution to these problems and is now being hurried, vaccines are only effective in preventing infections by specific viruses because of their specificity. Since vaccine production is a process requiring a considerable amount of time, it is often difficult to reserve required amounts of a particular vaccine. Thus, there is a strong demand for antiviral agents that show antiviral activity against a wide range of viruses.

Viruses are divided into those that are encapsulated in a lipid-containing membrane called an envelope and those that are not. Since an envelope is mostly composed of lipid, it can easily be destroyed by treating with ethanol, organic solvents, soap and other disinfectants. For this reason, viruses with an envelope can easily be inactivated by these disinfectants (i.e., reduction or elimination of the ability to infect). To the contrary, viruses without an envelope are considered to be highly resistant to these disinfectants. As used herein, the terms "virus inactivation activity" and "antiviral activity" both refer to the same activity.

To address the above-described issues, inorganic antiviral agents that have a wider spectrum of activity than organic viral agents have been developed. For example, a fabric impregnated with an antimicrobial dye agent and divalent copper ion is reported to have the ability to inactivate influenza virus (Patent Document 1). Also, an antiviral fiber formed of carboxyl-containing fiber impregnated with a copper compound is reported (Patent Document 2). Furthermore, a cold-worked ultrafine copper fiber effective in inactivating avian influenza virus is reported (Patent Document 3). Use of other elements for inactivation of viruses, for example, use of a titanium oxide photocatalyst, is also reported (Patent Documents 4 and 5).

PRIOR ART DOCUMENTS

Patent Documents

Patent Document 1 Japanese Patent Application Laid-Open No. 2006-188499
Patent Document 2 International Patent Publication No. WO05/083171 pamphlet
Patent Document 3 Japanese Patent Application Laid-Open No. 2008-138323
Patent Document 4 Japanese Patent Application Laid-Open No. 2005-160494
Patent Document 5 Japanese Patent Application Laid-Open No. 2009-072430

SUMMARY OF THE INVENTION

Problems to be Solved by the Invention

However, the approach by divalent copper ion requires that the copper ion be stabilized by being mixed with other materials. As a result, the proportion of copper ion in the composition is limited. In other words, it is essential that the composition contain a stabilizer of divalent copper ion. This results in a decreased degree of freedom in the design of the composition. The approach by carboxyl-containing fiber impregnated with a copper compound requires salts, in addition to the carboxyl groups. This limits the amount of the copper compound that can be carried by the fiber, thus leading to insufficient antiviral performance. Also, the approach by metal copper requires a special washing process to keep the antiviral activity that is otherwise lost by dirt or dust sticking to the surface. This makes the approach undesirably complex and impractical. The approach by titanium oxide and other photocatalysts is also disadvantageous in that the photocatalysts require strong UV radiation to exhibit their activity and their activation of the ability for inactivation may take a long time if the amount of UV radiation is insufficient.

To solve the above-described problems, the present invention provides an antiviral agent that can inactivate viruses, as well as products that include such an antiviral agent.

Means for Solving the Problems

A first invention concerns an antiviral agent, containing as an active ingredient particles of at least one kind of iodide composed of iodine and an element shown in Period 4 to Period 6 and Group 8 to Group 15 of a periodic table.

A second invention concerns the antiviral agent of the first invention above, wherein the element shown in Period 4 to Period 6 and Group 8 to Group 15 of the periodic table is Cu, Ag, Sb, Ir, Ge, Sn, Tl, Pt, Pd, Bi, Au, Fe, Co, Ni, Zn, In or Hg.

A third invention concerns the antiviral agent of the second invention above, wherein the iodide is at least one selected from the group consisting of CuI, AgI, SbI$_3$, InI$_4$, GeI$_4$, GeI$_2$, SnI$_2$, SnI$_4$, TlI, PtI$_2$, PtI$_4$, PdI$_2$, BiI$_3$, AuI, AuI$_3$, FeI$_2$, CoI$_2$, NiI$_2$, ZnI$_2$, HgI and InI$_3$.

A fourth invention concerns an antiviral agent, containing as an active ingredient particles of at least one kind of monovalent copper compound.

A fifth invention concerns the antiviral agent of the fourth invention above, wherein the monovalent copper compound is a chloride, an acetate, a sulfide, an iodide, a bromide, a peroxide, an oxide or a thiocyanide.

A sixth invention concerns the antiviral agent of the fifth invention above, wherein the monovalent copper compound is at least one selected from the group consisting of CuCl, CuOOCCH$_3$, CuBr, CuI, CuSCN, Cu$_2$S and Cu$_2$O.

A seventh invention concerns a fiber structure, containing the antiviral agent of the first to the sixth invention above or having the antiviral agent of the first to the sixth invention immobilized to the outer surface thereof.

An eighth invention concerns a molded article, containing the antiviral agent of the first to the sixth invention above or having the antiviral agent of the first to the sixth invention immobilized to the outer surface thereof.

A ninth invention concerns a film or sheet, containing the antiviral agent of the first to the sixth invention above or having the antiviral agent of the first to the sixth invention immobilized to the outer surface thereof.

Effects of the Invention

According to the present invention, there is provided an antiviral agent that can inactivate viruses, as well as a product including such an antiviral agent.

BEST MODE FOR CARRYING OUT THE INVENTION

The antiviral agent of the present embodiment contains as an active ingredient either particles of at least one kind of iodide composed of iodine and an element shown in Period 4 to Period 6 and Group 8 to Group 15 of a periodic table or particles of at least one kind of monovalent copper compound.

Although the mechanism by which the antiviral agent of the present invention inactivates viruses is still unclear at present, it is believed that as the iodide or the monovalent copper compound of the present embodiment comes into contact with viruses, it acts on viral DNA or RNA to inactivate the DNA or RNA or destroys the cytoplasm. The monovalent copper compound is also believed to inactivate viruses as follows: as monovalent copper ions generated upon exposure of the monovalent copper compound to the atmospheric moisture are converted into more stable divalent copper ions, electrons are released and this electron transfer affects the electrical charges on the surface of the viruses, inactivating them.

The iodide or the monovalent copper compound to serve as the active ingredient of the antiviral agent of the present embodiment exhibits antiviral activity without being mixed with, for example, a stabilizer. In other words, the antiviral agent of the present embodiment can be designed more freely in terms of its constituents as compared to conventional antiviral agents.

In addition, since the antiviral agent of the present embodiment does not require any stabilizers or the like to be mixed with it, it can be produced in a simple manner without requiring any pretreatments of antiviral components. Furthermore, the antiviral agent of the present embodiment is stable when dispersed in a dispersion medium such as air and water, so that no special washing process is required. Thus, the antiviral agent can readily exhibit and maintain its antiviral activity.

Because many of the iodides and monovalent copper compounds for use in the present embodiment are already widely commercially available, these compounds, if chemically stable, can be used in a wide range of applications in a relatively simple manner, for example, by kneading with resins or mixing with paints.

The at least one kind of iodide for use in the present embodiment having antiviral activity is composed of iodine and an element shown in Period 4 to Period 6 and Group 8 to Group 15 of a periodic table. It is preferred that the element in Period 4 to Period 6 and Group 8 to Group 15 of a periodic table be Cu, Ag, Sb, Ir, Ge, Sn, Tl, Pt, Pd, Bi, Au, Fe, Co, Ni, Zn, In or Hg. It is more preferred that the particles of iodide contained in the antiviral agent of the present embodiment be particles of at least one selected from the group consisting of CuI, AgI, SbI$_3$, IrI$_4$, GeI$_4$, GeI$_2$, SnI$_2$, SnI$_4$, TlI, PtI$_2$, PtI$_4$, PdI$_2$, BiI$_3$, AuI, AuI$_3$, FeI$_2$, CoI$_2$, NiI$_2$, ZnI$_2$, HgI and InI$_3$.

It is also preferred that the monovalent copper compound for use in the present embodiment having antiviral activity be a chloride, an acetate, a sulfide, an iodide, a bromide, a peroxide, an oxide or a thiocyanide. It is more preferred that the particles of the monovalent copper compound contained in the antiviral agent of the present embodiment be particles of at least one selected from the group consisting of CuCl, CuOOCCH$_3$, CuBr, CuI, CuSCN, Cu$_2$S and Cu$_2$O.

Of the particles of the above-described iodides or monovalent copper compounds for use in the antiviral agent of the present embodiment, particles of at least one selected from the group consisting of CuI, AgI, SnI$_4$, CuCl, CuBr and CuSCN are particularly preferred because of their high storage stability in air.

Although the iodide or the monovalent copper compound for use in the present embodiment may have any particle size appropriately determined by a person skilled in the art, it is preferably provided in the form of fine particles having an average particle size of 500 µm or less. When the particles are to be kneaded with a resin for spinning into fibers, they preferably have an average particle size of 1 µm or less to avoid the decrease in the fiber strength. In the present embodiment, the particle size is preferably 1 nm or more in view of the production, handling and chemical stability of the particles, although the particles may have any particle size appropriately determined by a person skilled in the art. As used herein, the term "average particle size" refers to volume average particle size.

The antiviral agent of the present embodiment can be used to inactivate an unlimited range of viruses regardless of the type of their genome and whether the viruses have an envelope. Examples of such viruses include rhinovirus, poliovirus, rotavirus, norovirus, enterovirus, hepatovirus, astrovirus, sapovirus, hepatitis E virus, influenza A/B/C viruses, parainfluenza virus, mumps virus, measles virus, human metapneumovirus, RS virus, nipah virus, hendra virus, yellow fever virus, dengue virus, Japanese encephalitis virus, West Nile virus, hepatitis B/C viruses, Eastern and Western equine encephalitis viruses, O'nyong-nyong virus, rubella virus, Lassa virus, Junin virus, Machupo virus, Guanarito virus, Sabia virus, Crimean Congo hemorrhagic fever, sandfly fever, hantavirus, Sin Nombre virus, Rabies virus, Ebolavirus, Marburgvirus, bat lyssavirus, human T-cell leukemia virus, human immunodeficiency virus, human coronavirus, SARS coronavirus, human parvovirus, human polyomavirus, human papilloma virus, adenovirus, herpes virus, varicellovirus, herpes zoster virus, EB virus, cytomegalovirus, smallpox virus, monkeypox virus, cowpox virus, Molluscipoxvirus and parapoxvirus.

The antiviral agent of the present embodiment can be used in various forms. While from the viewpoint of handling, the antiviral agent of the present embodiment is most preferably used in the form of, for example, powder, it may be used in any other suitable form. For example, the antiviral agent may be dispersed in a dispersion medium such as water. When the antiviral agent of the present embodiment is dispersed in a dispersion medium, it is preferred that the dispersion contain 0.2 mass % or more of the iodide or monovalent copper compound, the active ingredient, to ensure sufficient antiviral activity. In the present embodiment, for example, the amount of the antiviral agent in the dispersion is preferably 30 mass % or less to ensure stability and handleability of the dispersion, although the dispersion may contain the antiviral agent in any suitable amount determined by a person skilled in the art. The antiviral agent of the present embodiment may be used in combination with a known antiviral agent such as ethanol and hypochlorous acid to enhance the desired effect. Also, the antiviral agent may be crystallized within or on the surface of a fiber or other substrates that are intended to contain the antiviral agent or have the antiviral agent immobilized thereto. Furthermore, the antiviral agent may be mixed with other antiviral agents, antimicrobial agents, anti-mold agents, anti-allergen agents, catalysts, anti-reflection materials or heat insulation materials.

In addition, the antiviral agent of the present embodiment may be provided in the form of a fiber structure that contains the antiviral agent or has the antiviral agent immobilized to its outer surface.

The antiviral agent of the present embodiment may be subjected to any treatment appropriately selected by a person skilled in the art for containment or immobilization of the antiviral agent to the fiber structure. For example, the antiviral agent of the present embodiment may be added to a polymer material and kneaded and spun into a fiber, so that the antiviral agent is contained in the fiber structure. Alternatively, the antiviral agent may be immobilized to a fiber structure such as woven fabric or nonwoven fabric using, for example, a binder. Also, the antiviral agent may be immobilized to an inorganic material such as zeolite, which in turn is immobilized to a fiber structure to form an antiviral fiber structure. As used herein, the phrase "antiviral agent is contained" is intended to include cases where the antiviral agent is exposed outside.

Specific examples of the fiber structure include a mask, an air conditioner filter, an air cleaner filter, clothes, an insect screen and a poultry house net. Examples of the polymer material to form the fiber structure include polyester, polyethylene, polypropylene, polyvinyl chloride, polyethylene terephthalate, polybutylene terephthalate, polytetramethylene terephthalate, nylon, acryl, polytetrafluoroethylene, polyvinyl alcohol, Kevlar, polyacrylic acid, poly(methylmethacrylate), rayon, cupra, tinsel, polynosic, acetate, triacetate, cotton, hemp, wool, silk and bamboo.

Moreover, the antiviral agent of the present embodiment may be provided in the form of a molded article that contains the antiviral agent or has the antiviral agent immobilized to its outer surface. As is the case with the fiber structure, the antiviral agent of the present embodiment may be subjected to any treatment appropriately selected by a person skilled in the art for containment or immobilization of the antiviral agent to the outer surface of a molded article. For example, when the molded article is formed of an organic material such as a resin, the antiviral agent may be kneaded with the resin before the resin is molded into the molded article. When the molded article is formed of an inorganic material such as a metal, the antiviral agent may be immobilized to the outer surface of the molded article using a binder. The molded article having the antiviral agent of the present embodiment can inactivate any virus that comes into contact with the molded article. For example, a telephone receiver that contains the antiviral agent of the present embodiment or has the antiviral agent immobilized to its outer surface can prevent an uninfected person who uses the receiver after an infected person from being infected with a virus.

As is the case with the above-described fiber structures and molded articles, the antiviral agent of the present invention may be provided in the form of a film or sheet that contains the antiviral agent or has the antiviral agent immobilized to its outer surface by using a similar immobilization technique by kneading or using a binder. Specific examples of the film or sheet include wall paper, wrapping bag and wrapping film. Viruses attached to the surface of these films or sheets are inactivated by the antiviral activity of the antiviral agent. Thus, hospital-acquired infection or contamination of medical instruments with viruses can be prevented by applying the above-described wall paper to the wall of hospital rooms, or by wrapping medical instruments with the above-described wrapping bag or wrapping film.

An antiviral fiber containing copper (I) iodide, an example of the particles of the iodide or the monovalent copper compound to provide the antiviral agent of the present embodiment, or having copper (I) iodide immobilized to its outer surface can be produced by various techniques, such as follows: a technique including having iodine adsorb onto a fiber, and treating the iodine-adsorbed fiber with an aqueous solution of a cuprous compound so that the resulting article contains copper (I) iodide; a technique including dispersing copper (I) iodide powder in a molten resin, and spinning the resin; a technique including dispersing copper (I) iodide powder in a polymer solution, and spinning the polymer solution; a technique using mechanical milling to immobilize copper (I) iodide powder to the surface of a fiber; and a technique using a coating agent to immobilize copper (I) iodide to the surface of a fiber. These techniques can be used with various polymer materials to form a polymer material containing copper (I) iodide or having copper (I) iodide immobilized to its outer surface at a wide range of concentration ranging from a low to high concentration.

The antiviral fiber containing the antiviral agent of the present embodiment preferably contains the iodide, the active ingredient, or has the iodide immobilized in an amount of 0.2 mass % or more relative to the antiviral fiber to achieve higher antiviral activity. While the maximum amount of the iodide contained in (or immobilized to) the antiviral fiber is not particularly limited and may be appropriately determined by a person skilled in the art, the antiviral fiber preferably contains the iodide in an amount of 80 mass % or less in order to ensure fiber strength and other physical properties of the antiviral fiber. The proportion of the iodide contained in the antiviral fiber can be measured by thermogravimetric analysis, titration, atomic absorption spectrometry or ICP analysis.

An antiviral fiber containing copper (I) chloride, an example of the monovalent copper compound, or having copper (I) chloride immobilized to its outer surface can be produced by various techniques, such as follows: a technique including adding and kneading copper (I) chloride with a molten polymer to disperse copper (I) chloride in the polymer, and subsequently forming the polymer into a fiber; a technique using mechanical milling to immobilize copper (I) chloride powder to the surface of a fiber; a technique using a coating agent to immobilize copper (I) chloride to the surface of a fiber; a technique including dispersing copper (I) chloride in a polymer dissolved in a solvent, and subsequently applying the dispersion to other material to immobilize copper (I) chloride; and a technique including dissolving copper (I) chloride in aqueous hydrochloric acid, immersing a hydrophilic polymer material such as Nylon 6 or polyacrylic acid in the aqueous solution to immobilize monovalent copper ions to the polymer material, and further immersing the polymer material in aqueous hydrochloric acid to crystallize copper (I) chloride. Alternatively, copper (I) chloride may be encapsulated by temperature-responsive poly(N-isopropylacrylamide) to form capsules, which in turn are used to form a fiber that contains the capsules or has the capsules immobilized to its outer surface.

Although it has been mentioned above that the antiviral fiber preferably contains copper iodide or has copper iodide immobilized in an amount of 0.2 mass % to 80 mass % relative to the antiviral fiber, other iodides or monovalent copper compounds for use in the present embodiment are also preferably contained in or immobilized to the antiviral fiber in an amount of 0.2 mass % to 80 mass % relative to the antiviral fiber for the same reasons as described above. It should be appreciated that the fiber structure also preferably contains the antiviral agent of the present embodiment or has the antiviral agent immobilized in an amount of 0.2 mass % to 80 mass % relative to the fiber structure.

EXAMPLES

While the present invention will now be described with reference to examples, the present invention is not limited to these examples only.

Evaluation of Antiviral Activity by Anti-HA Activity

Examples 1 to 27

Each of the commercially available powders of iodine compounds and monovalent copper compounds shown in Table 1 was suspended in 100 µl of MEM (Minimum Essential Medium Eagle, MP Biomedical) to suspension concentrations of 5 mass % and 0.5 mass % for evaluation of antiviral activity. As used herein, the term "suspension concentration" means the percentage by mass of a particular component (such as iodide or monovalent copper compound) of a suspension relative to the total mass (=100%) of all components forming the suspension, including the iodide or the monovalent copper compound and a solvent.

(Evaluation Method)

In a standard hemagglutination (HA) assay, the titer (HA titer) was determined for Examples 1 to 27 by visually observing complete agglutination. The virus used was influenza virus (influenza A/kitakyusyu/159/93 (H3N2)) cultured in MDCK cells.

Specifically, two-fold serial dilutions of a virus solution diluted with phosphate-buffered saline (PBS) were prepared and 50 µl of each dilution was added to the wells of a plastic 96-well plate. 50 µl of 0.5% chicken RBC suspension was then added to each well. The plate was left at 4° C. for 60 minutes and the HA titer was determined. The determined HA titer for this virus solution was 256.

Next, each of the substances of Examples shown in Table 1 was diluted with PBS to suspension concentrations of 10 mass % and 1 mass %. To 450 µL each of the two samples with the respective concentrations, 450 µL of the above virus solution determined to have an HA titer of 256 was added and the resulting suspension was reacted at room temperature for 10 minutes while being stirred with a microtube rotator. As a control, 450 µL of the virus solution having an HA titer of 256 was added to 450 µL of PBS and, like the other samples, the resulting solution was stirred for 10 minutes with the microtube rotator.

The solid component was then precipitated in an ultra-microcentrifuge and the supernatant was collected and used as a sample solution. Two-fold serial dilutions, 50 µL each, of the sample solution diluted with PBS were prepared. To each dilution, 50 µL of 0.5% chicken RBC suspension was added and the resulting suspension was left at 4° C. for 60 minutes and the HA titer was determined. The results are shown in Tablet. Each of the substances of Examples has concentrations of 5 mass % and 0.5 mass % in each reaction mixture because an equal amount of the virus solution was added to each sample.

TABLE 1

| Example No. | Name of substance | Molecular formula | Manufacturer (Retailer) | Quality/grade |
|---|---|---|---|---|
| 1 | Copper (I) iodide | CuI | Wako | Wako 1st grade |
| 2 | Silver (I) iodide | AgI | Wako | Chemical grade |
| 3 | Antimony (III) iodide | $SbI_3$ | Strem chemicals (Wako) | 99.90% |
| 4 | Iridium (IV) iodide | $IrI_4$ | Alfa Aesar (Wako) | 99.95% |
| 5 | Germanium (IV) iodide | $GeI_4$ | Alfa Aesar (Wako) | 99.999% |
| 6 | Germanium (II) iodide | $GeI_2$ | AlDRICH | 99.99% |
| 7 | Tin (II) iodide | $SnI_2$ | Alfa Aesar (Wako) | 99+% |
| 8 | Tin (IV) iodide | $SnI_4$ | Strem chemicals (Wako) | 95% |
| 9 | Thallium (I) iodide | TlI | Wako | Optical grade |
| 10 | Platinum (II) iodide | $PtI_2$ | Strem chemicals (Wako) | 99% |
| 11 | Platinum (IV) iodide | $PtI_4$ | Alfa Aesar (Wako) | 99.95% |
| 12 | Palladium (II) iodide | $PdI_2$ | Strem Chemicals, Inc. | |
| 13 | Bismuth (III) iodide | $BiI_3$ | Strem chemicals (Wako) | 99.999% |
| 14 | Gold (I) iodide | AuI | Strem chemicals (Wako) | (Wako) 99% |
| 15 | Gold (III) iodide | $AuI_3$ | ChemPur Feinchemikalien und Forschungsbedarf GmbH (Wako) | |
| 16 | Iron (II) iodide | $FeI_2$ | Aldrich | >99.99% |
| 17 | Cobalt (II) iodide | $CoI_2$ | Aldrich | 95% |
| 18 | Nickel (II) iodide | $NiI_2$ | Alfa Aesar (Wako) | 99.50% |
| 19 | Zinc (II) iodide | $ZnI_2$ | Wako | Wako 1st grade |
| 20 | Silver (I) iodide | HgI | Wako | Chemical grade |
| 21 | Indium (III) iodide | $InI_3$ | Alfa Aesar (Wako) | 99.999% |
| 22 | Copper (I) chloride | CuCl | Wako | Reagent special grade |
| 23 | Copper (I) bromide | CuBr | Wako | Wako 1st grade |
| 24 | Copper (I) acetate | $CuOOCCH_3$ | Tokyo Chemical Industry | 98% reagent |

TABLE 1-continued

| Example No. | Name of substance | Molecular formula | Manufacturer (Retailer) | Quality/grade |
|---|---|---|---|---|
| 25 | Copper (I) thiocyanate | CuSCN | Wako | Chemical grade |
| 26 | Copper (I) sulfate | $Cu_2S$ | Alfa Aesar (Wako) | 99.5% |
| 27 | Copper (I) oxide | $Cu_2O$ | Wako | 99.5+% |

(Note)
Wako = Wako Pure Chemical Industries

TABLE 2

| Example No. | Name of substance | Molecular formula | HA titer Conc. of substance (mass %) 5 | 0.5 |
|---|---|---|---|---|
| 1 | Copper (I) iodide | CuI | 8 | 32 |
| 2 | Silver (I) iodide | AgI | 32 | 64 |
| 3 | Antimony (III) iodide | $SbI_3$ | 16 | 32 |
| 4 | Iridium (IV) iodide | $IrI_4$ | 32 | 64 |
| 5 | Germanium (IV) iodide | $GeI_4$ | <2 | <2 |
| 6 | Germanium (II) iodide | $GeI_2$ | <2 | 2 |
| 7 | Tin (II) iodide | $SnI_2$ | <2 | 2 |
| 8 | Tin (IV) iodide | $SnI_4$ | <2 | 2 |
| 9 | Thallium (I) iodide | TlI | 32 | 64 |
| 10 | Platinum (II) iodide | $PtI_2$ | <2 | 64 |
| 11 | Platinum (IV) iodide | $PtI_4$ | 32 | 64 |
| 12 | Palladium (II) iodide | $PdI_2$ | 2 | 64 |
| 13 | Bismuth (III) iodide | $BiI_3$ | 8 | 64 |
| 14 | Gold (I) iodide | AuI | 4 | 64 |
| 15 | Gold (III) iodide | $AuI_3$ | 8 | 64 |
| 16 | Iron (II) iodide | $FeI_2$ | <2 | <2 |
| 17 | Cobalt (II) iodide | $CoI_2$ | <2 | 8 |
| 18 | Nickel (II) iodide | $NiI_2$ | <2 | 4 |
| 19 | Zinc (II) iodide | $ZnI_2$ | <2 | 4 |
| 20 | Silver (I) iodide | HgI | 32 | 64 |
| 21 | Indium (III) iodide | $InI_3$ | <2 | <2 |
| 22 | Copper (I) chloride | CuCl | <2 | <2 |
| 23 | Copper (I) bromide | CuBr | <2 | 32 |
| 24 | Copper (I) acetate | $CuOOCCH_3$ | <2 | <2 |
| 25 | Copper (I) thiocyanate | CuSCN | 16 | 64 |
| 26 | Copper (I) sulfate | $Cu_2S$ | 16 | 64 |
| 27 | Copper (I) oxide | $Cu_2O$ | 8 | 64 |
| Control | (PBS) | | 128 | |

(Note 1)
"<2" in table means the lowest HA titer that can be measured.
(Note 2)
Control is performed at 0% concentration (PBS alone).

The results of Table 2 indicate that each of the substances of Examples 1 to 27 has the ability to inactivate the virus. As shown, the HA titer is 32 or less for each substance at the concentration of 5%, indicating that 75% or more of the virus has been inactivated. In particular, each of the substances $GeI_4$, $GeI_2$, $SnI_2$, $SnI_4$, $PtI_2$, $FeI_2$, $CoI_2$, $NiI_2$, $ZnI_2$, $InI_3$, CuCl, CuBr and $CuOOCCH_3$ resulted in high activity of 99% or higher virus inactivation, which is the lowest value that can be detected by this assay.

(Evaluation of Antiviral Activity by the Inactivation of Influenza Virus and Feline Calicivirus)

As previously described, viruses are divided into those that are encapsulated in a lipid-containing membrane called an envelope and those that are not. Thus, the ability of test substances to inactivate an enveloped virus and a non-enveloped virus was evaluated. The enveloped virus used was influenza virus (influenza A/kitakyusyu/159/93 (H3N2)) and the non-enveloped virus used was feline calicivirus (F9 strain), a commonly used alternative to non-enveloped norovirus.

Examples 28 to 31

A commercially available powder of copper (I) iodide (Wako 1st grade, Wako Pure Chemical Industries) was suspended in 100 µl of a diluted MEM solution to suspension concentrations of 5 mass %, 1 mass %, 0.2 mass % and 0.1 mass %. The suspensions were designated as Examples 28, 29, 30 and 31, respectively, and the antiviral activity of each suspension against feline calicivirus and influenza virus was evaluated.

Example 32 to 35

A commercially available powder of copper (I) chloride (Wako special grade, Wako Pure Chemical Industries) was suspended in 100 µl of a diluted MEM solution to suspension concentrations of 2 mass %, 1 mass %, 0.5 mass % and 0.25 mass %. The suspensions were designated as Examples 32, 33, 34 and 35, respectively, and the antiviral activity of each suspension against feline calicivirus and influenza virus was evaluated.

(Evaluation Method of Antiviral Activity)

The antiviral activity of Examples 28 to 35 was evaluated by the plague assay that can detect a virus at high accuracy. Specifically, 100 µl of each virus solution was added to 100 µl of each test sample solution and to 100 µl of a diluted MEM solution as a blank. Each solution was reacted in an incubator at 25° C. while being agitated at 200 rpm. After a predetermined agitation period, 1800 µl of 20 mg/ml broth protein was added to terminate the reaction of the viruses with each compound in each sample. Each reaction sample was serially diluted to $10^{-2}$ to $10^{-5}$ with a diluted MEM solution (10 step dilution). After reaction, 100 µl each of the sample solutions of feline calicivirus was inoculated onto confluent CrFK cells and 100 µl each of the sample solutions of influenza virus was inoculated onto MDCK cells. After a 90-minute adsorption period, 0.7% agar medium was overlaid onto each plate. The plates inoculated with feline calicivirus were incubated for 48 hours and the plates inoculated with influenza virus were incubated for 64 hours in a 5% $CO_2$ incubator at 34° C. Subsequently, the cells were fixed with formalin and stained with methylene blue. The plaques were counted and the virus titer was calculated in plaque-forming units (PFU/0.1 ml, Log 10) as a measure of antiviral activity. The results are shown in Tables 3 and 4.

TABLE 3

| | | Virus titer (PFU/0,.1 ml, Log10) | | | | |
|---|---|---|---|---|---|---|
| | | Example 28 CuI 5% | Example 29 CuI 1% | Example 30 CuI 0.2% | Example 31 CuI 0.1% | Blank CuI 0% |
| Influenza virus | 1 min | <1 | <1 | 1.17 | 3.24 | 7.02 |
| | 10 min | <1 | <1 | <1 | 2.98 | 7.00 |
| Feline calicivirus | 1 min | <1 | <1 | 2.11 | 4.63 | 6.50 |
| | 10 min | <1 | <1 | 1.60 | 4.2 | 6.44 |

The results of Table 3 indicate that the copper (I) iodide powder exhibited sufficiently high virus inactivation activity both against enveloped influenza virus and non-enveloped strong feline calicivirus in a time period as short as 1 minute.

TABLE 4

| | | Virus titer (PFU/0,.1 ml, Log10) | | | | |
|---|---|---|---|---|---|---|
| | | Example 32 CuCl 2% | Example 33 CuCl 1% | Example 34 CuCl 0.5% | Example 35 CuCl 0.25% | Blank CuCl 0% |
| Influenza virus | 1 min | <1 | <1 | <1 | 1.12 | 7.02 |
| | 10 min | <1 | <1 | <1 | <1 | 7.00 |
| Feline calicivirus | 1 min | <1 | <1 | <1 | 1.05 | 6.50 |
| | 10 min | <1 | <1 | <1 | <1 | 6.44 |

The results of Table 4 indicate that the copper (I) chloride powder exhibited sufficiently high virus inactivation activity both against enveloped influenza virus and non-enveloped strong feline calicivirus in a time period as short as 1 minute.

The results of Tables 3 and 4 demonstrate that Examples 28 and 29, each iodide composed of an element in Period 4 to Period 6 and Group 8 to Group 15 of a periodic table, and Examples 32 to 34, each a monovalent copper compound, caused the influenza virus to decrease to one-millionth or less and the feline calicivirus to one-three hundred thousandth or less of the initial number upon exposure to the viruses in a time period as short as 1 minute. Thus, the inactivation rate, or antiviral activity, of these compounds was extremely high for both viruses: 99.9999% or more for influenza virus and 99.999% or more for feline calicivirus.

As used herein, the term "inactivation rate" is a value defined by the following equation:

$$\text{Inactivation rate}(\%) = 100 \times (10^{\text{Virus titer of blank}} - 10^{\text{Virus titer of sample}}) / 10^{\text{Virus titer of blank}} \quad \text{(Mathematical Equation 1)}$$

As set forth, the antiviral agent of the present invention exhibit remarkably high and immediate effect regardless of the type of virus, so that many applications can be contemplated by introducing or immobilizing the antiviral agent to various substrates. Thus, the antiviral agent of the present invention should find practical applications.

The invention claimed is:

1. A method of inactivating an influenza virus, which comprises immobilizing to an outer surface of an article a viral inactivating amount of an antiviral agent comprising particles of at least one kind of monovalent copper compound, wherein the monovalent copper compound is a chloride, an acetate, a sulfide, an iodide, a bromide, a peroxide, or a thiocyanide, and contacting the article having the immobilized antiviral agent with the influenza virus, wherein the influenza virus is inactivated.

2. The method according to claim 1, wherein the monovalent copper compound is at least one selected from the group consisting of $CuCl$, $CuOOCCH_3$, $CuBr$, $CuI$, $CuSCN$, and $Cu_2S$.

3. The method of claim 1, wherein the article has a fiber structure.

4. The method of claim 1, wherein the article is a molded article.

5. The method of claim 1, wherein the article is a film or sheet.

6. The method according to claim 1, wherein the average particle size of the particles of monovalent copper compound is 1 nm or more and 500 μm or less.

* * * * *